United States Patent [19]

Thunberg et al.

[11] 3,932,501

[45] Jan. 13, 1976

[54] PROCESS FOR RECOVERING BETA-ALANINE FROM SODIUM CHLORIDE SOLUTIONS

[75] Inventors: Jon Carl Thunberg, Amherst, N.H.; Robert Wright Bragdon, Marblehead, Mass.; William Philip Moore, Hudson, N.H.

[73] Assignee: W. R. Grace & Co., New York, N.Y.

[22] Filed: Mar. 25, 1975

[21] Appl. No.: 561,924

Related U.S. Application Data

[63] Continuation-in-part of Ser. No. 517,469, Oct. 24, 1974, which is a continuation-in-part of Ser. No. 442,543, Feb. 14, 1974, abandoned, which is a continuation-in-part of Ser. No. 319,539, Dec. 29, 1972, Pat. No. 3,808,269.

[52] U.S. Cl. ............................................. 260/534 C
[51] Int. Cl.² .......................................... C07C 99/12
[58] Field of Search ..................... 260/534 C, 534 R

[56] References Cited
UNITED STATES PATENTS
3,433,832    3/1969    Swanson .......................... 260/534 R

*Primary Examiner*—Vivian Garner
*Attorney, Agent, or Firm*—Elton Fisher

[57] ABSTRACT

β-alanine is recovered from a starting solution of sodium chloride and β-alanine by: (a) evaporating water from the solution to precipitate sodium chloride and form a first mother liquor; (b) separating the first mother liquor and the precipitated sodium chloride while the first mother liquor is hot; (c) cooling the separated first mother liquor to precipitate β-alanine and form a second mother liquor; (d) separating the precipitated β-alanine and the second mother liquor; and (e) recovering the separated β-alanine.

If desired, the separated second mother liquor can be admixed with a second lot of the starting solution and processed therewith.

9 Claims, No Drawings

PROCESS FOR RECOVERING BETA-ALANINE FROM SODIUM CHLORIDE SOLUTIONS

CROSS REFERENCE TO RELATED APPLICATIONS

This is a continuation-in-part of copending application Ser. No. 517,469, filed Oct. 24, 1974. Said application Ser. No. 517,469 is a continuation-in-part of application Ser. No. 442,543, filed Feb. 14, 1974, and now abandoned. Said application Ser. No. 442,543 is a continuation-in-part of application Ser. No. 319,539, filed Dec. 29, 1972, and now U.S. Pat. No. 3,808,269. The benefit of said earlier filed applications is claimed.

BACKGROUND OF THE INVENTION

This invention is in the field of $\beta$-alanine. More specifically, this invention is directed to a process for preparing pure or substantially pure $\beta$-alanine.

In the prior art amino acids have been prepared by: (a) hydrolyzing the corresponding nitrile with an aqueous alkaline earth metal hydroxide to form an alkaline earth metal salt of the amino acid; and (b) treating the alkaline earth metal salt with carbon dioxide to form the free amino acid (which remains in solution) and an alkaline earth metal carbonate (which precipitates). The amino acid is then recovered. This method, as applied to the preparation of $\beta$-alanine, is taught by "Organic Syntheses", collective volume 3, pp. 34–36, John Wiley and Sons, Inc., 1955.

It is desirable to replace the alkaline earth metal hydroxide of the prior art with sodium hydroxide because the latter has a lower equivalent weight than strontium and barium hydroxides, is more soluble, is easier to handle under plant conditions, and the ions of sodium, unlike those of barium, (a preferred alkaline earth metal hydroxide) are not toxic. However, such substitution introduces a complication in the separation and recovery of the amino acid ($\beta$-alanine) because sodium carbonate, unlike the alkaline earth metal carbonates, is readily soluble in water, thereby to render to separation and recovery of pure or substantially pure $\beta$-alanine difficult.

A method for separating certain free amino acids from a system comprising the amino acid, sodium chloride, and water is taught by U.S. Pat. No. 3,433,832 (Swanson et al, 260/534).

The Swanson et al method is not applicable to amino acids such as $\beta$-alanine which have a solubility greater than 35.0 parts per 100 parts of water at 100°C. The process of our invention has been found to present an effective and convenient method for recovering $\beta$-alanine from a system consisting essentially of water, $\beta$-alanine, and sodium chloride. Such a system results where the amino acid ($\beta$-alanine) is formed from the corresponding nitrile by hydrolysis with sodium hydroxide followed by treatment with hydrochloric acid to convert the intermediate sodium salt (sodium $\beta$-alaninate (sodium $\beta$-aminopropionate)) to the free amino acid ($\beta$-alanine).

SUMMARY OF THE INVENTION

In summary, this invention is directed to a process for recovering $\beta$-alanine from an aqueous starting solution consisting essentially of water, $\beta$-alanine, and sodium chloride, the aqueous starting solution having a temperature above 0°C (e.g., between about 0.5°C and about its normal boiling point or between about 5°C and 100°C), a pH of 4.5–8.5, and a mole ratio of $\beta$-alanine to sodium chloride of 0.7–5:1, or 1–5:1 or 0.7–3:1, the process comprising (or consisting essentially of):

a. forming a first slurry consisting essentially of a first lot of precipitated solid sodium chloride and a first mother liquor consisting essentially of water, dissolved $\beta$-alanine, and dissolved sodium chloride by evaporating water from the aqueous starting solution;

b. separating the first mother liquor from the first lot of precipitated solid sodium chloride at a temperature effective for preventing the precipitation of solid $\beta$-alanine (e.g., within a temperature range between about 60°C and the normal boiling point of the second slurry (e.g., about 70°–100°C or 80°–95°C));

c. forming a second slurry consisting essentially of a first lot of precipitated solid $\beta$-alanine and a second mother liquor consisting essentially of water, dissolved $\beta$-alanine, and dissolved sodium chloride by adjusting the temperature of the separated first mother liquor to a temperature effective for precipitating $\beta$-alanine (e.g., to a temperature within a range of about 0.5°–55°C, or 5°–50°C, or 10°–30°C, or to any temperature between about 0.5°C and about 55°C) if the separated first mother liquor is above such temperature;

d. separating the second mother liquor from the first log of precipitated solid -alanine while maintaining the temperature of the second slurry within a temperature range effective for precipitating $\beta$-alanine (e.g., to a temperature within a range of about 0.5°–55°C, or 5°–50°C, or 10°–30°C, or to any temperature between about 0.5°C and about 55°C); and e. recovering the separated $\beta$-alanine.

DESCRIPTION OF PREFERRED EMBODIMENTS

In preferred embodiments of the process of the above Summary:

1. The pH of the aqueous starting solution is 4.5–8.5 or 5.5–6.5 If the pH of the starting solution is not within the desired range (4.5–8.5 or 5.5–6.5), it can be brought to this range by adding caustic soda or a sodium salt of the amino acid to increase the pH, or HCl to lower the pH.

2. The mole ratio of $\beta$-alanine to sodium chloride in the aqueous starting solution is 0.7–2:1.

3. The starting solution analyzes (contains) 34–43% $\beta$-alanine.

In another preferred embodiment, ("Embodiment A") this invention is directed to a process for recovering $\beta$-alanine from an aqueous starting solution consisting essentially of water, $\beta$-alanine, and sodium chloride, the aqueous starting solution having a temperature above 0°C (e.g., between about 0.5°C and about its normal boiling point or between about 5°C and 100°C), a pH of 4.5–8.5, and a mole ratio of $\beta$-alanine to sodium chloride of 0.7–5:1, or 1–5:1 or 0.7–3:1, the process comprising (or consisting essentially of):

a. forming a first slurry consisting essentially of a first lot of precipitated solid sodium chloride and a first mother liquor consisting essentially of water, dissolved $\beta$-alanine, and dissolved sodium chloride by evaporating water from the aqueous starting solution;

b. separating the first mother liquor from the first lot of precipitated solid sodium chloride at a temperature effective for preventing the precipitation of solid $\beta$-alanine (e.g., within a temperature range between about 60°C and the normal boiling point of the second slurry (e.g., about 70°–100°C or

80°–95°C));

c. forming a second slurry consisting essentially of a first lot of precipitated solid β-alanine and a second mother liquor consisting essentially of water, dissolved β-alanine, and dissolved sodium chloride by adjusting the temperature of the separated first mother liquor to a temperature effective for precipitating β-alanine (e.g., to a temperature within a range of about 0.5°–55°C, or 5°–50°C, or 10°–30°C, or to any temperature between about 0.5°C and about 55°C) if the separated first mother liquor is above such temperature;

d. separating the second mother liquor from the first lot of precipitated solid β-alanine while maintaining the temperature of the second slurry within a temperature range effective for precipitating β-alanine (e.g., to a temperature within a range of about 0.5°–55°C, or 5°–50°C, or 10°–30°C, or to any temperature between about 0.5°C and about 55°C);

e. forming a third slurry consisting essentially of a second lot of precipitated solid sodium chloride and a third mother liquor consisting essentially of water, dissolved β-alanine and dissolved sodium chloride by admixing the separated second mother liquor with a second lot of the aqueous starting solution to form an aqueous system and evaporating water from the aqueous system;

f. separating the third mother liquor from the second lot of precipitated solid sodium chloride at a temperature effective for preventing the precipitation of solid β-alanine (e.g., within a temperature range between about 60°C and the normal boiling point of the second slurry (e.g., about 70°–100°C or 80°–95°C));

g. forming a fourth slurry consisting essentially of a second lot of precipitated solid β-alanine and a fourth mother liquor consisting essentially of water, dissolved β-alanine, and dissolved sodium chloride by adjusting the temperature of the separated third mother liquor to a range effective for precipitating β-alanine (e.g., to a temperature within the range of about 0.5°–55°C, or 5°–50°C, 10°–30°C, or to any temperature between about 0.5°C and about 55°C); and h. separating the second lot of precipitated solid β-alanine from the fourth mother liquor at a temperature effective for precipitating β-alanine (e.g., to a temperature within a range of about 0.5°–55°C, or 5°–50°C, or 10°–30°C, or to any temperature between about 0.5°C and about 55°C).

Steps (e), (f), (g), and (h), supra, can be repeated indefinitely by admixing the separated fourth mother liquor obtained in step (h) with a third (or subsequent) lot of aqueous starting solution (as recited in step (e)) and proceeding as recited in steps (e) through (h).

Where carrying on a long series of such runs (wherein steps (e) through (h) are repeated many times) it is generally preferred to remove a small portion of the fourth mother liquor (e.g., about 1–10% or 3–6% of the fourth mother liquor) to prevent the build up of color bodies and other undesired side-products which are present in small amounts in the aqueous starting solution. This removed portion is not admixed with starting aqueous solution in a repetition of step (e). It (the removed portion) can be discarded or processed separately to produce crude solid β-analine which can be used as such or purified by conventional techniques such as recrystallization.

In steps (a) and/or (e) the evaporation can be conducted at temperatures (e.g., below about 55° or 60°C) at which β-alanine can be precipitated along with the sodium chloride during the evaporation step providing steps (b) and/or (f), respectively, are conducted at temperatures above about 60°C so that any β-alanine which precipitated in steps (a) or (e) is redissolved and is not separated from the mother liquor along with the precipitated solid sodium chloride.

In certain embodiments of the invention of Embodiment A:

1. The mole ratio of amino acid (β-alanine) to sodium chloride in the aqueous starting solution is 1–5:1.

2. The pH of the aqueous starting solution is 4.5–8.5 or 5.5–6.5. If the pH of the aqueous starting solution is not within the desired range (e.g., 4.5–8.5 or 5.5–6.5), it can be adjusted and brought within this range by methods which are within the skill of those of ordinary skill in the art (e.g., by adding hydrochloric acid to lower the pH or by adding NaOH or the sodium salt of β-alanine to increase the pH).

3. The separated third mother liquor or about 80–99% (preferably 95–97% thereof) is combined with separated first mother liquor from another run or with a fresh lot of the aqueous starting solution and the resulting mixture is processed.

4. The aqueous starting solution is prepared by reacting the sodium salt of the amino acid (β-alanine) with an amount of hydrochloric acid effective to convert the salt of the amino acid to free amino acid (β-alanine) and sodium chloride. The sodium salt of the amino acid is preferably prepared by reacting a nitrile ($H_2NCH_2CH_2CN$) with an amount of aqueous sodium hydroxide solution effective for converting the nitrile to the sodium salt of the amino acid.

DETAILED DESCRIPTION OF THE INVENTION

If highly pure amino acid (β-alanine) is desired, the recovered (product) amino acid can be dissolved in hot water and recrystallized therefrom by cooling to form a solid phase consisting essentially of the recrystallized amino acid and a liquid phase consisting essentially of a solution of the amino acid in water. The solid phase (amino acid) can be separated from the liquid phase and recovered. At least a portion (e.g., up to about 80–99%, or 90–98%, or 100%) of the liquid phase from which the solid phase was separated can be admixed with the aqueous starting solution in a subsequent run.

Because of our disclosure it will be readily apparent to those skilled in the art that water can be evaporated from the aqueous solutions of the above Summary or Embodiment A at a reduced pressure (i.e., a pressure under 760 mm of mercury absolute) at normal atmospheric pressure, or at an elevated pressure (i.e., a pressure greater than 760 mm of mercury absolute). However, no particular advantage is gained by using reduced or elevated pressures and we generally prefer to operate at atmospheric pressure.

Because of our disclosure it will be readily understood by those skilled in the art that aqueous starting solutions containing considerably more than 5% amino acid are preferred for use in the process of our invention because less water will have to be evaporated to cause the sodium chloride to precipitate where using starting solutions containing appreciably more than 5% amino acid. Starting solutions containing about 20% or more amino acid are generally preferred. Obviously, starting solutions containing less than 5% amino acid or 1% or less amino acid can be used, but large amounts of water must be evaporated where using such solutions.

Aqueous starting slurries in which sodium chloride is present as a solid phase can be used in place of aqueous starting solutions. Where using such slurries we generally prefer to heat the slurry to a temperature effective to prevent the precipitation of the amino acid and to dissolve any precipitated amino acid before separating the solid sodium chloride. If necessary, additional water can be added to dissolve any solid amino acid present in the starting slurry.

We prefer to prepare our amino acid (β-alanine) from the corresponding nitrile according to the following sequence of reactions:

H$_2$NCH$_2$CH$_2$CN + H$_2$O + NaOH = H$_2$NCH$_2$CH$_2$COONa + NH$_3$

H$_2$NCH$_2$CH$_2$COONa + HCl = H$_2$NCH$_2$CH$_2$COOH + NaCl.

Where an excess of sodium hydroxide is added in the saponification step sufficient hydrochloric acid is added in the acidification step to neutralize such excess (free) sodium hydroxide according to the following equation:

NaOH + HCl = NaCl + H$_2$O.

The pH can be adjusted during (or after) the acidification step to a level (pH 4.5–8.5 or 5.5–6.5 or 6) preferred for separating the amino acid.

If too much hydrochloric acid is added during the acidification step or where adjusting the pH, the pH can be increased by neutralizing the excess acid with sodium hydroxide or with the sodium salt of the amino acid.

While it is preferred that the starting solution from which the amino acid (β-alanine) is recovered contain at least 5% amino acid, this value (5%) is not critical, and excellent results can be obtained with solutions containing less than about 5% of the amino acid. Solutions containing substantially less than 5% of the amino acid can be concentrated by evaporating water therefrom to bring their amino acid content to about 5%.

Of course, if the solution were evaporated too far and the concentration of the amino acid became too high, the amino acid would precipitate out at an elevated temperature. However, by noting the solubility of the amino acid (β-alanine) as a function of temperature, one skilled in the art can, because of this disclosure, readily avoid conditions under which the amino acid precipitates at elevated temperatures. For example, the solubility of β-alanine in water is 45.8% at 35°C and 54.9% at 80°C.

β-alanine separated by the process of this invention can, if desired, be washed, for example, with cool or cold water (e.g., water having the temperature of about 5°–25°C or up to about 30°C) or, alternatively, with a solution of the amino acid (e.g., a saturated or nearly saturated aqueous solution of said amino acid).

The instant invention will be better understood by referring to the following specific but nonlimiting procedures which illustrate a preferred method for conducting the process of this invention. It is understood that said invention is not limited by these procedures which are offered merely as illustrations; it is also understood that modifications can be made without departing from the spirit and scope of the invention.

PROCEDURE 1

(Preparation of Aqueous β-alanine-Sodium Chloride Solution)

50 moles of β-aminopropionitrile (H$_2$NCH$_2$CH$_2$CN) is saponified at 50°C with 51 moles of 20% sodium hydroxide solution. The product is boiled free of ammonia, bleached with hydrogen peroxide to remove undesired side-product color bodies, and diluted to 13.99 Kg. The resulting aqueous solution is acidified with 51 moles of 36% hydrochloric acid. The resulting solution which weighs 19.06 Kg and has a pH of 6 is an aqueous solution of β-alanine (23.4%), sodium chloride (15.6%), and water. This solution is designated "Solution 1".

PROCEDURE 2

(Recovery of β-alanine - First Cycle)

A 1,282 gram portion of Solution 1 is boiled to evaporate water therefrom. When 547 g of water has been evaporated the resulting slurry which is a slurry of solid crystalline sodium chloride in a first mother liquor consisting essentially of water, dissolved sodium chloride, and dissolved β-alanine, is cooled to about 80°C and centrifuged to separate the precipitated (solid phase crystalline) sodium chloride from the first mother liquor.

The separated first mother liquor is cooled to about 25°C and stirred for about 2 hours to form a second slurry consisting essentially of precipitated crystalline β-alanine and a second mother liquor consisting essentially of water, dissolved β-alanine, and dissolved sodium chloride.

The second slurry is centrifuged at bout 25°C to separate the precipitated crystalline β-alanine from the second mother liquor.

The separated second mother liquor is designated "Solution 2".

PROCEDURE 3

(Recovery of β-alanine - Second Cycle)

All of Solution 2 is admixed with a second 1,282 g portion of Solution 1 to form a resulting mixture which is boiled to evaporate water therefrom and to form a third slurry consisting essentially of precipitated crystalline sodium chloride and a third mother liquor consisting essentially of water, dissolved β-alanine, and dissolved sodium chloride. After 632 g of water has been evaporated from the third slurry, said slurry is cooled to about 80°C and centrifuged to separate the precipitated crystalline sodium chloride from the third mother liquor.

The separated third mother liquor is cooled to about 25°C and gently agitated (stirred) at said temperature for about 2 hours. This results in a formation of a fourth slurry consisting essentially of precipitated crystalline β-alanine and a fourth mother liquor consisting essentially of water, dissolved β-alanine, and dissolved sodium chloride.

The fourth slurry is centrifuged at about 25°C to separate the precipitated crystalline β-analine from the fourth mother liquor.

The separated crystalline β-alanine is recovered, dried and weighed. It weighs 167 g.

The separated fourth mother liquor is designated "Solution 3".

PROCEDURES 4 – 11

(Recovery of β-alanine - 3rd - 10th Cycles)

The general method of Procedure 3 is repeated in 8 replications (e.g., Cycles 3-10). However, in these runs, the method of Procedure 3 is modified by:

a. evaporating the quantities of water listed in Table 1 from the respective resulting mixtures to precipitate sodium chloride.

b. admixing separated fourth mother liquor from the second cycle and Solution 1 to prepare a resulting mixture for use in the third cycle.

In runs 5–11 (4th–10th cycles) the fourth mother liquor is as shown in Table 2.

TABLE 1

| Water Evaporated from the Resulting Mixture | | |
|---|---|---|
| Procedure No. | Cycle No. | Water Evaporated, g |
| 4 | 3 | 670 |
| 5 | 4 | 705 |
| 6 | 5 | 715 |
| 7 | 6 | 740 |
| 8 | 7 | 718 |
| 9 | 8 | 726 |
| 10 | 9 | 726 |
| 11 | 10 | 731 |

TABLE 2

| Fourth Mother Liquor Used in Procedures 4–11 (Cycles 3–10) | | |
|---|---|---|
| Procedure No. | Cycle No. | Separated Fourth Mother Liquor Mixed with Solution 1 to Prepare Resulting Mixture |
| 5 | 4 | Fourth Mother Liquor from Procedure 4 |
| 6 | 5 | Fourth Mother Liquor from Procedure 5 |
| 7 | 6 | Fourth Mother Liquor from Procedure 6* |
| 8 | 7 | Fourth Mother Liquor from Procedure 7* |
| 9 | 8 | Fourth Mother Liquor from Procedure 8* |
| 10 | 9 | Fourth Mother Liquor from Procedure 9* |
| 11 | 10 | Fourth Mother Liquor from Procedure 10* |

*In each of Procedures 8, 9, 10, and 11 (Cycles 7, 8, 9, and 10) an amount of separated fourth mother liquor from the previous procedure containing about 24 g of β-alanine is discarded before mixing such fourth separated mother liquor with Solution 1 to prepare resulting mixture for use in the next cycle (i.e., in Cycles 7, 8, 9, and 10, respectively).

Table 3 shows the amount of β-alanine and the amount of sodium chloride which is recovered in each of the above-described ten cycles (Procedures 2–11, Cycles 1–10).

TABLE 3

| β-alanine and Sodium Chloride Recovery | | | |
|---|---|---|---|
| Procedure No. | Cycle No. | β-alanine Recovery g | NaCl Recovery g |
| 2 | 1 | 112 | 129 |
| 3 | 2 | 167 | 158 |
| 4 | 3 | 212 | 159 |
| 5 | 4 | 268 | 161 |
| 6 | 5 | 266 | 201 |
| 7 | 6 | 289 | 182 |
| 8 | 7 | 272 | 206 |
| 9 | 8 | 279 | 185 |
| 10 | 9 | 273 | 190 |
| 11 | 10 | 280 | 180 |
| | Total | 2,318* | 1,751* |

*These totals do not include 97 g of β-alanine and 36 g of NaCl discarded in the discarded portions of separated fourth mother liquor from Cycles 6, 7, 8, and 9 (which are discarded before preparing resulting mixture for use in Cycles 7, 8, 9, and 10). Neither do they include 485 g of β-alanine and 181 g of NaCl present in the separated fourth mother liquor which is present at the end of Cycle 10. Such mother liquor (that obtained from Run 11 (Cycle 10)) or a portion of it can be used to prepare a resulting mixture for use in an eleventh cycle.

As shown in Table 3, total β-alanine recovered from Procedures 2 through 10 (i.e., from Cycles 1-10, supra) 2,318 g corresponding to 80.6% of the β-alanine charged and 1,751 g corresponding to 98.0% of the sodium chloride present are recovered. These values are exclusive of the 485 g of β-alanine and 181 g of NaCl present in the separated fourth mother liquor from Procedure 11 (10th cycle) and the 97 g of β-alanine and 36 g of NaCl discarded in separated fourth mother liquor from Procedures 7, 8, 9, and 10 (Cycles 6, 7, 8, and 9). Including these amounts in a balance sheet shows that 100% of the β-alanine charged in Cycles 1 through 10 and 98.0% of the NaCl charged in said cycles are accounted for.

The solid components (β-alanine or sodium chloride, respectively) of the slurries formed in the process of our invention can be separated from the respective mother liquors by filtration, decantation, or centrifugation.

β-alanine is an article of commerce. It is used as a starting material in the synthesis of pantothenic acid (a vitamin) and salts and other derivatives thereof.

As used herein the term "percent (%)" means parts per hundred and parts means parts by weight unless otherwise defined where used.

As used herein the term "mole" has its generally accepted meaning. A mole of a substance is that quantity which contains the same number of molecules of the substance as there are atoms in 12 grams of pure $^{12}C$.

As used herein the term "g" means gram or grams and the term "Kg" means kilogram or kilograms. A kilogram is 1000 grams.

We claim:

1. A process for recovering β-alanine from an aqueous starting solution consisting essentially of water, β-alanine, and sodium chloride, the aqueous starting solution having a temperature above 0°C, a pH of 4.5–8.5, and a mole ratio of β-alanine to sodium chloride of 0.7–5:1, the process comprising:

a. forming a first slurry consisting essentially of a first lot of precipitated solid sodium chloride and a first mother liquor consisting essentially of water, dissolved β-alanine, and dissolved sodium chloride by evaporating water from the aqueous starting solution;

b. separating the first mother liquor from the first lot of precipitated solid sodium chloride at a temperature effective for preventing the precipitation of solid β-alanine;

c. forming a second slurry consisting essentially of a first lot of precipitated solid β-alanine and a second mother liquor consisting essentially of water, dissolved β-alanine, and dissolved sodium chloride by adjusting the temperature of the separated first mother liquor to a temperature effective for precipitating β-alanine; and d. separating the second mother liquor from the first lot of precipitated solid β-alanine while maintaining the temperature of the second slurry within a temperature range effective for precipitating β-alanine, and recovering the separated β-alanine.

2. The process of claim 1 in which the pH of the aqueous starting solution is 5.5–6.5.

3. The process of claim 1 in which the mole ratio of β-alanine to sodium chloride in the aqueous starting solution is 1–5:1.

4. The process of claim 1 in which the aqueous starting solution contains 34–43% β-alanine.

5. A process for recovering β-alanine from an aqueous starting solution consisting essentially of water, β-alanine, and sodium chloride, the aqueous starting solution having a temperature above 0°C, a pH of 4.5–8.5 and a mole ratio of β-alanine to sodium chloride of 0.7–5:1, the process comprising:

a. forming a first slurry consisting essentially of a first lot of precipitated solid sodium chloride and a first mother liquor consisting essentially of water, dissolved β-alanine, and dissolved sodium chloride by evaporating water from the aqueous starting solution;

b. separating the first mother liquor from the first lot of precipitated solid sodium chloride at a temperature effective for preventing the precipitation of solid β-alanine;

c. forming a second slurry consisting essentially of a first lot of precipitated solid β-alanine and a second mother liquor consisting essentially of water, dissolved β-alanine, and dissolved sodium chloride by adjusting the temperature of the separated first mother liquor to a temperature effective for precipitating β-alanine;

d. separating the second mother liquor from the first lot of precipitated solid β-alanine while maintaining the temperature of the second slurry within a temperature range effective for precipitating β-alanine;

e. forming a third slurry consisting essentially of a second lot of precipitated solid sodium chloride and a third mother liquor consisting essentially of water, dissolved β-alanine and dissolved sodium chloride by admixing the separated second mother liquor with a second lot of the aqueous starting solution to form an aqueous system and evaporating water from the aqueous system;

f. separating the third mother liquor from the second lot of precipitated solid sodium chloride at a temperature effective for preventing the precipitation of solid β-alanine;

g. forming a fourth slurry consisting essentially of a second lot of precipitated solid β-alanine and a fourth mother liquor consisting essentially of water, dissolved β-alanine, and dissolved sodium chloride by adjusting the temperature of the separated third mother liquor to a range effective for precipitating β-alanine; and h. separating the second lot of precipitated solid β-alanine from the fourth mother liquor at a temperature effective for precipitating β-alanine.

6. The process of claim 5 in which the mole ratio of β-alanine to sodium chloride in the aqueous starting solution is 1–5:1.

7. The process of claim 5 in which the pH of the aqueous starting solution is 5.5–6.5.

8. The process of claim 5 in which the aqueous starting solution is prepared by reacting a sodium salt of β-alanine with an amount of hydrochloric acid effective to convert the salt to free β-alanine and sodium chloride.

9. The process of claim 8 in which the sodium salt of β-alanine is prepared by reacting $H_2NCH_2CH_2CN$ with an aqueous sodium hydroxide solution.

* * * * *